US009907683B2

(12) United States Patent
Zukowski et al.

(10) Patent No.: US 9,907,683 B2
(45) Date of Patent: Mar. 6, 2018

(54) CONTROLLED DEPLOYABLE MEDICAL DEVICE AND METHOD OF MAKING THE SAME

(71) Applicant: W. L. Gore & Associates, Inc., Newark, DE (US)

(72) Inventors: Stanislaw L. Zukowski, Flagstaff, AZ (US); Edward H. Cully, Flagstaff, AZ (US); Keith M. Flury, Flagstaff, AZ (US); Michelle L. Gendron, Flagstaff, AZ (US); Patrick S. Young, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 568 days.

(21) Appl. No.: 14/531,697

(22) Filed: Nov. 3, 2014

(65) Prior Publication Data
US 2015/0051691 A1 Feb. 19, 2015

Related U.S. Application Data

(63) Continuation of application No. 12/478,245, filed on Jun. 4, 2009, now abandoned.

(60) Provisional application No. 61/058,770, filed on Jun. 4, 2008.

(51) Int. Cl.
| | |
|---|---|
| *A61F 2/962* | (2013.01) |
| *A61F 2/97* | (2013.01) |
| *A61F 2/954* | (2013.01) |
| *A61F 2/07* | (2013.01) |
| *A61F 2/95* | (2013.01) |
| *A61F 2/89* | (2013.01) |

(52) U.S. Cl.
CPC ............. *A61F 2/954* (2013.01); *A61F 2/07* (2013.01); *A61F 2/95* (2013.01); *A61F 2/97* (2013.01); *A61F 2/89* (2013.01); *A61F 2002/072* (2013.01); *A61F 2002/075* (2013.01); *A61F 2002/9505* (2013.01); *A61F 2002/9511* (2013.01)

(58) Field of Classification Search
CPC .................................. A61F 2/95–2/97; A61F 2002/9505–2002/9665
See application file for complete search history.

(56) References Cited

U.S. PATENT DOCUMENTS

| | | | |
|---|---|---|---|
| 4,738,666 A | 4/1988 | Fuqua | |
| 5,387,235 A | 2/1995 | Chuter | |
| 5,405,378 A | 4/1995 | Strecker | |
| 5,464,449 A * | 11/1995 | Ryan | A61F 2/07 600/36 |

(Continued)

FOREIGN PATENT DOCUMENTS

| | | |
|---|---|---|
| EP | 664107 | 1/1995 |
| EP | 956833 | 11/1999 |

(Continued)

*Primary Examiner* — Victor Nguyen
*Assistant Examiner* — Jonathan Hollm

(57) ABSTRACT

Controlled deployable medical devices that are retained inside a body passage and in one particular application to vascular devices used in repairing arterial dilations, e.g., aneurysms. Such devices can be adjusted during deployment, thereby allowing at least one of a longitudinal or radial re-positioning, resulting in precise alignment of the device to an implant target site.

18 Claims, 6 Drawing Sheets

(56) References Cited

U.S. PATENT DOCUMENTS

| | | |
|---|---|---|
| 5,554,183 A | 9/1996 | Nazari |
| 5,643,279 A | 7/1997 | Trotta |
| 5,662,702 A | 9/1997 | Keranen |
| 5,683,451 A | 11/1997 | Lenker et al. |
| 5,693,083 A | 12/1997 | Baker et al. |
| 5,713,948 A * | 2/1998 | Uflacker ............... A61F 2/07 606/194 |
| 5,776,186 A | 7/1998 | Uflacker |
| 5,800,521 A | 9/1998 | Orth |
| 5,824,055 A | 10/1998 | Spiridigliozzi et al. |
| 5,843,158 A | 12/1998 | Lenker et al. |
| 5,957,929 A | 9/1999 | Brennemen |
| 6,042,605 A | 3/2000 | Martin et al. |
| 6,051,001 A | 4/2000 | Borghi |
| 6,168,616 B1 | 1/2001 | Brown, III |
| 6,235,051 B1 | 5/2001 | Murphy |
| 6,245,097 B1 | 6/2001 | Inoue |
| 6,251,132 B1 | 6/2001 | Ravenscroft et al. |
| 6,270,520 B1 | 8/2001 | Inoue |
| 6,280,464 B1 | 8/2001 | Hayashi |
| 6,287,315 B1 | 9/2001 | Wijeratne et al. |
| 6,302,891 B1 | 10/2001 | Nadal |
| 6,352,561 B1 | 3/2002 | Leopold et al. |
| 6,361,637 B2 | 3/2002 | Martin et al. |
| 6,371,979 B1 | 4/2002 | Beyar et al. |
| 6,416,536 B1 | 7/2002 | Yee |
| 6,520,986 B2 | 2/2003 | Martin et al. |
| 6,533,811 B1 | 3/2003 | Ryan et al. |
| 6,551,350 B1 | 4/2003 | Thornton et al. |
| 6,558,396 B1 | 5/2003 | Inoue |
| 6,565,597 B1 | 5/2003 | Fearnot et al. |
| 6,656,212 B2 | 12/2003 | Ravenscroft et al. |
| 6,676,692 B2 | 1/2004 | Rabkin et al. |
| 6,723,116 B2 | 4/2004 | Taheri |
| 6,776,791 B1 | 8/2004 | Stallings et al. |
| 6,821,291 B2 | 11/2004 | Bolea et al. |
| 6,837,901 B2 | 1/2005 | Rabkin et al. |
| 6,852,116 B2 | 2/2005 | Leonhardt et al. |
| 6,855,159 B1 * | 2/2005 | Tanner ............... A61B 17/0469 606/108 |
| 6,916,335 B2 | 7/2005 | Kanji |
| 6,945,990 B2 | 9/2005 | Greenan |
| 6,984,244 B2 | 1/2006 | Perez et al. |
| 7,074,235 B1 | 7/2006 | Roy |
| 7,226,473 B2 | 6/2007 | Brar |
| 8,043,356 B2 | 10/2011 | Kolbel et al. |
| 2002/0038144 A1 | 3/2002 | Trout et al. |
| 2002/0099431 A1 | 7/2002 | Armstrong et al. |
| 2002/0161377 A1 | 10/2002 | Rabkin |
| 2002/0161427 A1 | 10/2002 | Rabkin et al. |
| 2002/0188344 A1 | 12/2002 | Bolea et al. |
| 2003/0004560 A1 | 1/2003 | Chobotov et al. |
| 2003/0135269 A1 | 7/2003 | Swanstrom |
| 2003/0199966 A1 | 10/2003 | Shiu et al. |
| 2003/0225446 A1 | 12/2003 | Hartley |
| 2004/0087965 A1 | 5/2004 | Levine et al. |
| 2004/0093058 A1 | 5/2004 | Cottone et al. |
| 2004/0093063 A1 | 5/2004 | Wright et al. |
| 2004/0138734 A1 | 7/2004 | Chobotov et al. |
| 2004/0143316 A1 | 7/2004 | Spiridigliozzi et al. |
| 2004/0147939 A1 | 7/2004 | Rabkin et al. |
| 2004/0210298 A1 | 10/2004 | Rabkin et al. |
| 2004/0220655 A1 | 11/2004 | Swanson et al. |
| 2004/0230287 A1 | 11/2004 | Hartley et al. |
| 2004/0260383 A1 | 12/2004 | Stelter et al. |
| 2005/0038495 A1 | 2/2005 | Greenan |
| 2005/0060018 A1 | 3/2005 | Ditman |
| 2005/0085890 A1 | 4/2005 | Rassmussen et al. |
| 2005/0090834 A1 | 4/2005 | Chiang et al. |
| 2005/0107862 A1 | 5/2005 | Ohlenschlaeger |
| 2005/0119722 A1 * | 6/2005 | Styrc ............... A61F 2/95 623/1.12 |
| 2005/0182290 A1 | 8/2005 | Lau et al. |
| 2005/0182476 A1 | 8/2005 | Hartley et al. |
| 2006/0004433 A1 | 1/2006 | Greenberg et al. |
| 2006/0036314 A1 | 2/2006 | Perez et al. |
| 2006/0184226 A1 | 8/2006 | Austin |
| 2006/0190075 A1 | 8/2006 | Jordan et al. |
| 2006/0229699 A1 | 10/2006 | Tehrani |
| 2006/0259119 A1 | 11/2006 | Rucker |
| 2006/0259122 A1 | 11/2006 | Eliseev |
| 2006/0276872 A1 | 12/2006 | Arbefeuille et al. |
| 2007/0010875 A1 | 1/2007 | Trout et al. |
| 2007/0016281 A1 | 1/2007 | Melsheimer |
| 2007/0043425 A1 | 1/2007 | Hartley et al. |
| 2007/0043432 A1 | 2/2007 | Perouse |
| 2007/0088424 A1 | 4/2007 | Greenberg et al. |
| 2007/0100427 A1 | 5/2007 | Peruse |
| 2007/0142894 A1 | 6/2007 | Moore et al. |
| 2007/0225797 A1 * | 9/2007 | Krivoruhko ............... A61F 2/07 623/1.35 |

FOREIGN PATENT DOCUMENTS

| | | |
|---|---|---|
| EP | 1842508 | 10/2007 |
| EP | 1923024 | 5/2008 |
| FR | 2 896 405 | 1/2006 |
| JP | 2005-179587 | 5/2005 |
| JP | 2005-537107 | 12/2005 |
| JP | 2008-119481 | 5/2008 |
| WO | 1995/001761 | 1/1995 |
| WO | 1997/003624 | 2/1997 |
| WO | 2001060285 | 8/2001 |
| WO | 2004/021932 | 3/2004 |
| WO | 2006/134258 | 12/2006 |
| WO | 2007/025101 | 3/2007 |
| WO | 2008/029296 | 3/2008 |
| WO | 2008/042266 | 4/2008 |

* cited by examiner

US 9,907,683 B2

CONTROLLED DEPLOYABLE MEDICAL DEVICE AND METHOD OF MAKING THE SAME

BACKGROUND OF THE INVENTION

Field of the Invention

The invention relates generally to devices that are retained inside a body passage and in one particular application to vascular devices used in repairing arterial dilations, e.g., aneurysms. More particularly, the invention is directed toward devices that can be adjusted during deployment, thereby allowing at least one of a longitudinal or radial re-positioning of the device.

Discussion of the Related Art

The invention will be discussed generally with respect to deployment of a bifurcated stent graft into the abdominal aorta but is not so limited and may apply to device deployment into other body lumens. When delivering a stent graft by intraluminal or endovascular methods, it is important to know the precise location of the device in the vasculature. Controlling this precise location is particularly important when the device is intended to be deployed in close proximity to branch vessels or adjacent to weakened portions of the aortic wall. Typical stent grafts used to repair an aortic aneurysm incorporate a proximal (i.e. portion of the stent graft closest to the heart) anchoring system intended to limit longitudinal displacement of the stent graft. Often this anchoring system must be precisely placed to avoid occlusion of a branch vessel or to avoid placement within a compromised and damaged portion of the aortic wall.

An improved delivery system for such stent grafts would include a means for allowing precise longitudinal and rotational placement of the stent graft and anchoring system. The precise position of the stent graft and anchoring system would be adjusted and visualized prior to full deployment of the device. Ideally the delivery system would allow the device to be repositioned if the prior deployment position was undesirable.

SUMMARY OF THE INVENTION

The present invention is directed to a controlled deployable medical device and method of making the same that substantially obviates one or more of the problems due to limitations and disadvantages of the related art.

An embodiment of the present invention provides an apparatus, comprising a catheter having a proximal end portion and distal end portion. A hub can be arranged on a distal end portion of the catheter. A stent member is arranged on the proximal end portion of the catheter, the stent member has an inner surface and an outer surface. The stent can be configured in any suitable manner. In an embodiment of the invention, the stent is configured from multiple turns of an undulating element. Such a stent member can have substantially in-phase undulations. A graft member can be arranged about the stent member. Moreover, an element can be connected to a torsional member, wherein the torsional member is capable of retracting a portion of the element and thereby radially compressing at least a portion of the stent.

In another embodiment, the present invention provides an apparatus substantially as described above, further comprising a tube having a proximal end portion and distal end portion arranged on at least a portion of the substantially tubular shaped stent member, wherein at least a portion of the torsional member extends within a portion of the tube.

BRIEF DESCRIPTION OF THE DRAWINGS

The accompanying drawings are included to provide a further understanding of the invention and illustrate certain aspects of the invention.

In the drawings.

DETAILED DESCRIPTION OF THE ILLUSTRATED EMBODIMENTS

Figure 1A:
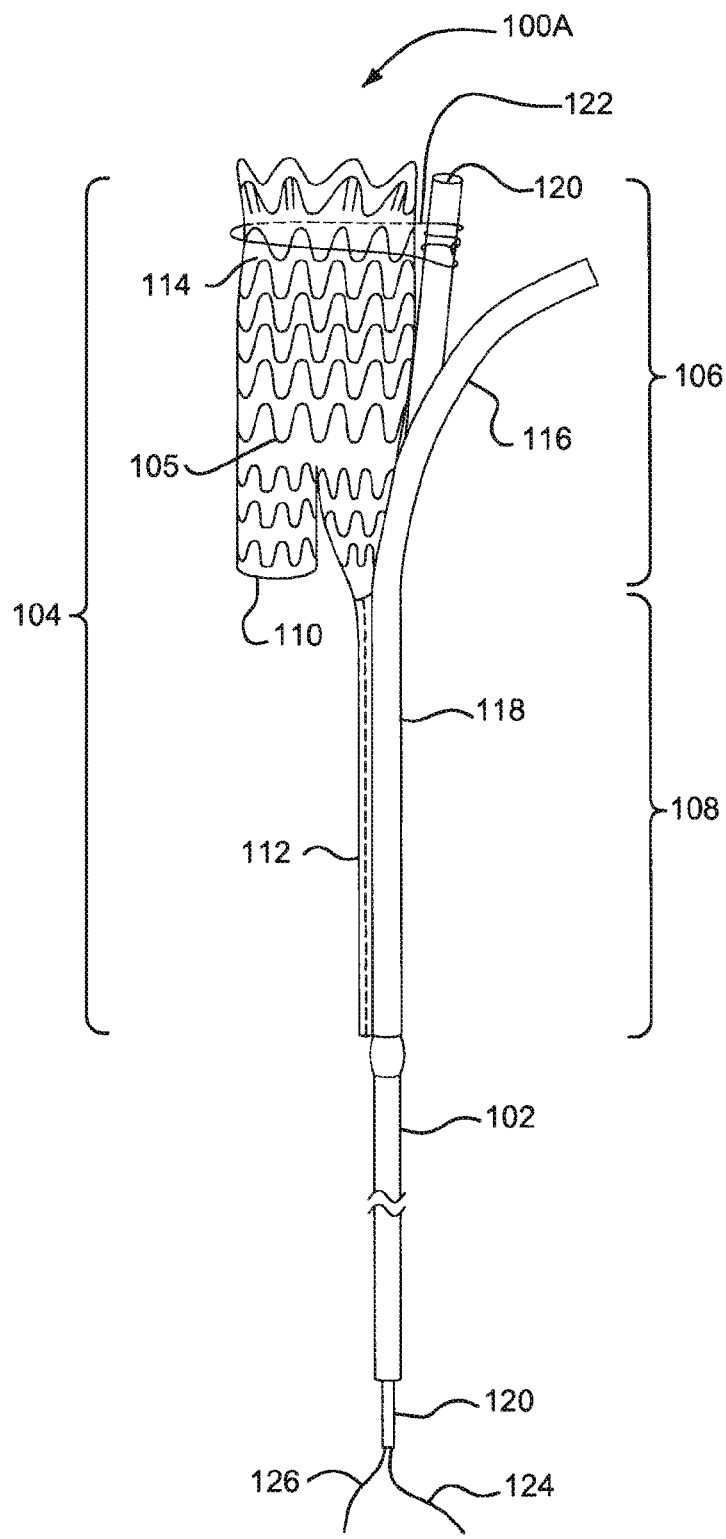
FIG. 1A is a medical apparatus according to an aspect of the invention, having an external torsional member.

The invention relates generally to a novel medical apparatus that includes a device capable of being retained inside a body passage and in one particular application to vascular devices. More particularly, the invention is directed toward devices that can be adjusted during deployment, thereby allowing at least one of a longitudinal or radial re-positioning. The term distal as used herein denotes a position furthest from the heart, while the term proximal denotes a position closest to the heart.

In an embodiment of the invention, the medical apparatus includes a catheter assembly having a proximal end portion and distal end portion. A hub can be optionally arranged on a distal end portion of the catheter assembly. A stent is arranged on a proximal end portion of the catheter. A graft member can be arranged about at least a portion of the stent. The stent may be self-expandable, balloon-expandable or a combination of self-expandable and balloon-expandable.

In some embodiments, the stents can be used to fix the medical apparatus inside a portion of a patient's anatomy. The stent can be preferably constructed from materials that are flexible and strong. The stent can be formed from degradable bioabsorable materials, biodigestible materials, polymeric materials, metallic materials and combinations thereof. In addition, these materials may be reinforced and/or coated with other materials, such as polymeric materials and the like. The coating may be chosen to reduce acidic or basic effects of the gastrointestinal tract, e.g., with a thermoplastic coating such as ePTFE and the like.

More specifically, the stents can be fabricated according to the methods and materials as generally disclosed in, for example, U.S. Pat. No. 6,042,605 issued to Martin, et al., U.S. Pat. No. 6,361,637 issued to Martin, et al. and U.S. Pat. No. 6,520,986 issued to Martin, et al. For example, stents can have various configurations as known in the art and can be fabricated, for example, from cut tubes, wound wires (or ribbons), flat patterned sheets rolled into a tubular form, combinations thereof, and the like. Stents can be formed from metallic, polymeric or natural materials and can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyvinylchloride, polyurethane, elastomeric organosilicon polymers; metals such as stainless steels, cobalt-chromium alloys and nitinol and biologically derived materials such as bovine arteries/veins, pericardium and collagen. Stents can also comprise bioresorbable materials such as poly(amino acids), poly(anhydrides), poly(caprolactones), poly(lactic/glycolic acid) polymers, poly(hydroxybutyrates) and poly(orthoesters).

The stents can be formed into a variety of different geometric configurations having constant and/or varied thickness as known in the art. The geometric configurations may include many conventional stent configurations such as a helically wrapped stent, z-shape stent, tapered stent, coil stent, combinations thereof, and the like. The stents can be formed in a variety of patterns, such as, a helix pattern, ring pattern, combinations thereof, and the like.

Grafts can have various configurations as known in the art and can be fabricated, for example, from tubes, sheets or films formed into tubular shapes, woven or knitted fibers or ribbons or combinations thereof. Graft materials can include, for example, conventional medical grade materials such as nylon, polyester, polyethylene, polypropylene, polytetrafluoroethylene, polyvinylchloride, polyurethane and elastomeric organosilicone polymers.

Stents can be used alone or in combination with graft materials. Stents can be configured on the external or internal surface of a graft or may be incorporated into the internal wall structure of a graft. Stent or stent grafts can be delivered endoluminally by various catheter based procedures known in the art. For example self-expanding endoluminal devices can be compressed and maintained in a constrained state by an external sheath. The sheath can be folded to form a tube positioned external to the compressed device. The sheath edges can be sewn together with a deployment cord that forms a "chain stitch". To release and deploy the constrained device, one end of the deployment cord can be pulled to disrupt the chain stitch, allowing the sheath edges to separate and release the constrained device. Constraining sheaths and deployment cord stitching can be configured to release a self-expanding device in several ways. For example a constraining sheath may release a device starting from the proximal device end, terminating at the distal device end. In other configurations the device may be released starting from the distal end. Self expanding devices may also be released from the device center as the sheath disrupts toward the device distal and proximal ends.

Details relating to constraining sheath materials, sheath methods of manufacture and stent graft compression techniques can be found in, for example, U.S. Pat. No. 6,352,561 issued to Leopold, et al., and U.S. Pat. No. 6,551,350 issued to Thornton, et al.

The catheter and hub assemblies can comprise conventional medical grade materials such as nylon, polyacrylamide, polycarbonate, polyethylene, polyformaldehyde, polymethylmethacrylate, polypropylene, polytetrafluoroethylene, polytrifluorochlorethylene, polyether block amide or thermoplastic copolyether, polyvinylchloride, polyurethane, elastomeric organosilicone polymers, and metals such as stainless steels and nitinol.

Figure 1B:
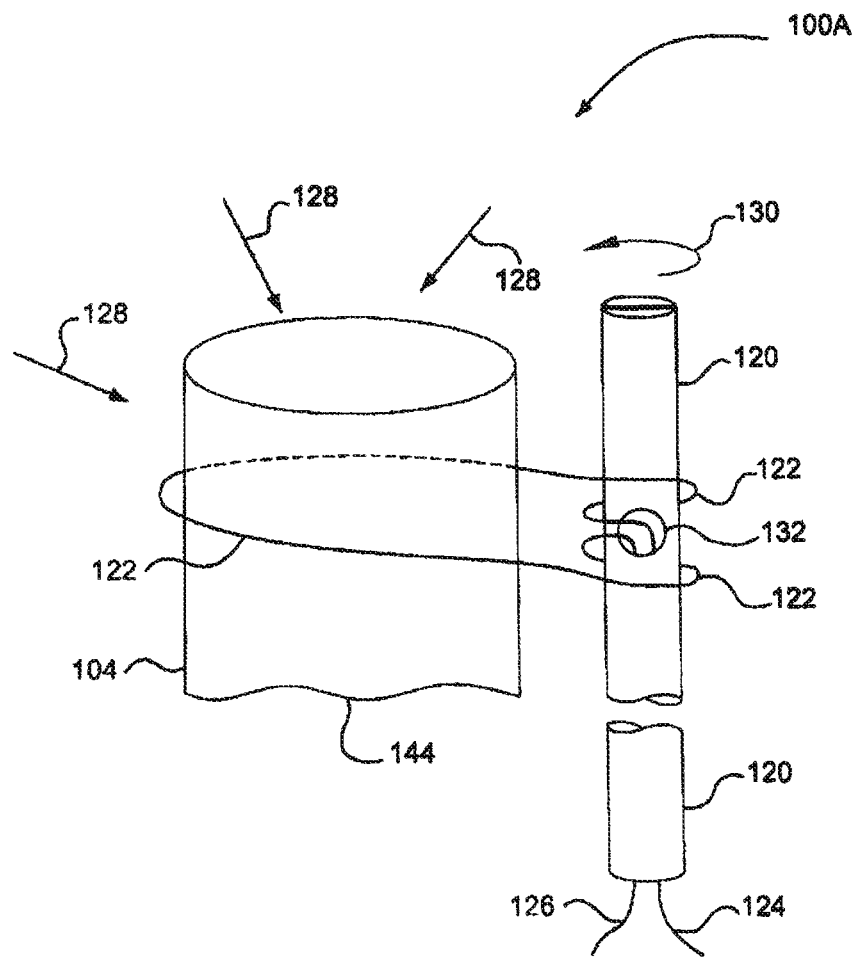
FIG. 1B is an enlarged simplified view of the medical apparatus of FIG. 1A according to an aspect of the invention.

Turning to the figures, FIG. 1A is a medical apparatus according to an embodiment of the invention. FIG. 1B is an enlarged simplified view of a portion of the medical apparatus shown in FIG. 1A.

Referring to FIGS. 1A and 1B, the medical apparatus is generally depicted as reference numeral 100A. The medical apparatus 100A includes catheter assembly 102, stent 104 arranged on the proximal end portion of the catheter assembly 102. The stent 104 has an inner surface, an outer surface, and is configured from multiple turns of an undulating element 105. The undulating element 105 can be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

In an embodiment of the invention, the stent 104 and graft member 114 are constrained into a compacted delivery state by a first sheath 116 and second sheath 118. As shown in FIG. 1A, the first sheath 116 has been released allowing at least a portion of the stent 104 to expand as shown. The second sheath 118 is coupling the second leg 112 to the catheter assembly 102 as shown.

A torsional member 120 extends from a proximal end portion to a distal end portion of the catheter assembly 102. In the figure, the torsional member 120 is positioned adjacent the outer surface of the stent 104 and graft 114. The torsional member 120 is attached to the catheter assembly 102 and not attached to the stent 104 or graft 114. A movable element 122 having a first end 124 and second end 126 surrounds the stent 104 and graft member 114. The first end 124 and second end 126 of the movable element 122 extend out a distal end portion of the torsional member 120. For example, the movable element 122 is threaded through the tube from a distal end to a proximal end and is looped around the proximal end portion 106 of the stent 104 and graft member 114.

As shown in FIG. 1B, the torsional member 120 can be rotated in the direction shown by arrow 130, tensioning the movable element 122 thereby causing at least a portion of the stent/graft to radial compress in the direction indicated by arrows 128. The torsional member 120 can be configured with a side-wall aperture 132 through which the two ends 124, 126 of the movable element 122 can be routed. The torsional member 120 can be rotated by turning the distal end of the tube 120. The torsional member 120 can be rotated in the opposite direction (of that shown by arrow 130) to allow the stent/graft to expand in the direction opposite of arrows 128. The stent/graft can be compressed to allow rotational or longitudinal displacements within a vessel. When the desired placement is verified, the stent/graft can be allowed to expand and engage the vessel wall. Repeated compressions and expansions of the stent/graft can be utilized as desired. The stent/graft can also be gradually compressed or allowed to gradually expand by varying the amount of twist imparted to the torsional member 120. After final placement of the stent/graft, tension can be applied to one of the ends 124, 126 of the moveable element 122 to release and withdraw the movable element.

Figure 1C:
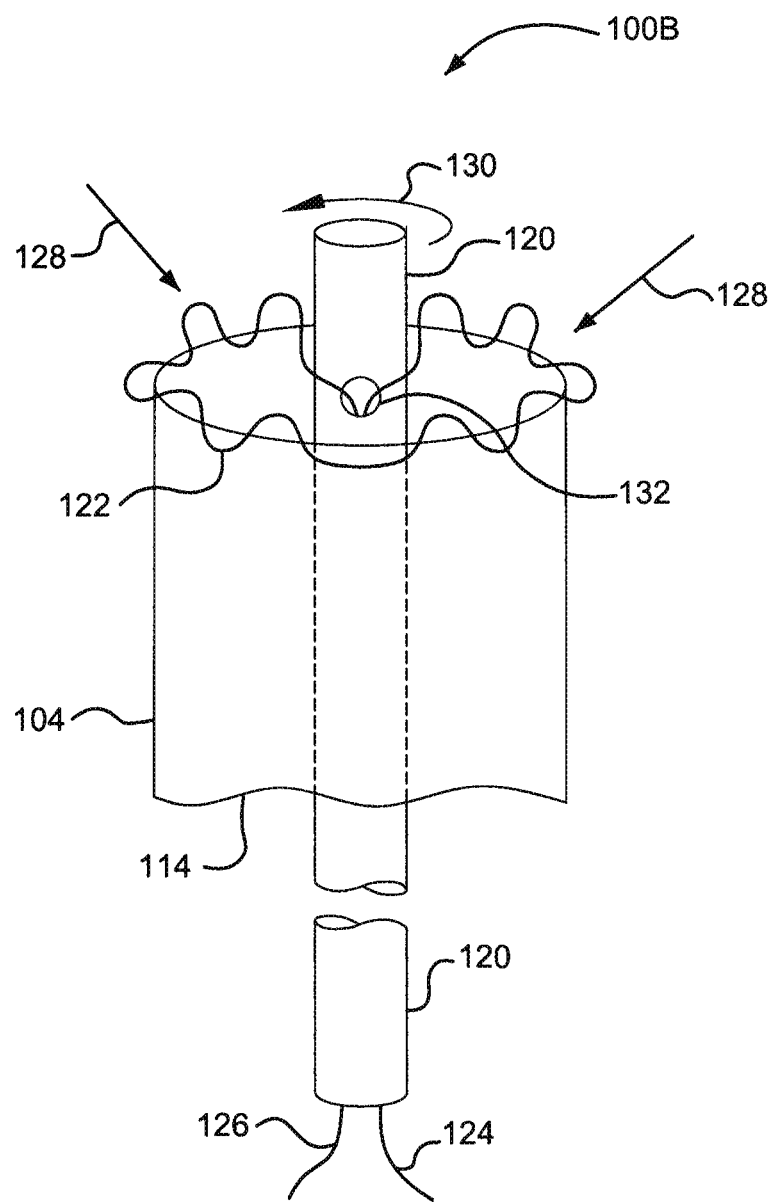
FIG. 1C is a medical apparatus according to an aspect of the invention, having an internal torsional member.

FIG. 1C is a medical apparatus according to a further embodiment of the invention, having a torsional member 120 positioned internal to the stent/graft.

Referring to FIG. 1C, the medical apparatus is generally depicted as reference numeral 100B. The medical apparatus of FIG. 1C is similar to the medical apparatus as shown in FIGS. 1A and 1B. The medical apparatus includes a stent 104 and/or a graft 114 arranged on the proximal end portion of the catheter assembly.

A torsional member 120 extends from a proximal end portion to a distal end portion of the catheter assembly. The torsional member 120 is positioned internal to the stent 104 and graft 114. The torsional member 120 is attached to the catheter assembly and not attached to the stent 104 or graft 114. A movable element 122 having a first end 124 and second end 126 is looped through and around the stent 104 and graft member 114. The first end 124 and second end 126 of the movable element 122 extend out a distal end portion of the torsional member 120. For example, the movable element 122 is threaded through the tube from a distal end to a proximal end and is looped around the proximal end portion of the stent 104 and graft member 114. As shown in FIG. 1C, the torsional member 120 can be rotated in the direction shown by arrow 130, tensioning the movable element 122 thereby causing at least a portion of the stent/graft to radial compress in the direction indicated by arrows 128. The torsional member 120 can be configured with a side-wall aperture 132 through which the two ends 124, 126 of the movable element 122 can be routed. The torsional member 120 can be rotated by turning the distal end of the torsional member 120. The torsional member 120 can be rotated in the opposite direction (of that shown by arrow 130) to allow the stent/graft to expand in the direction opposite of arrows 128. The stent/graft can be compressed to allow rotational or longitudinal displacements within a vessel. When the desired placement is verified, the stent/graft can be allowed to expand and engage the vessel wall. Repeated compressions and expansions of the stent/graft can be utilized as desired. The stent/graft can also be gradually compressed or allowed to gradually expand by varying the amount of twist imparted to the torsional member 120. After final placement of the stent/graft, tension can be applied to one of the moveable ends 124, 126 of the moveable element 122 to release and withdraw the movable element.

Figure 2B:
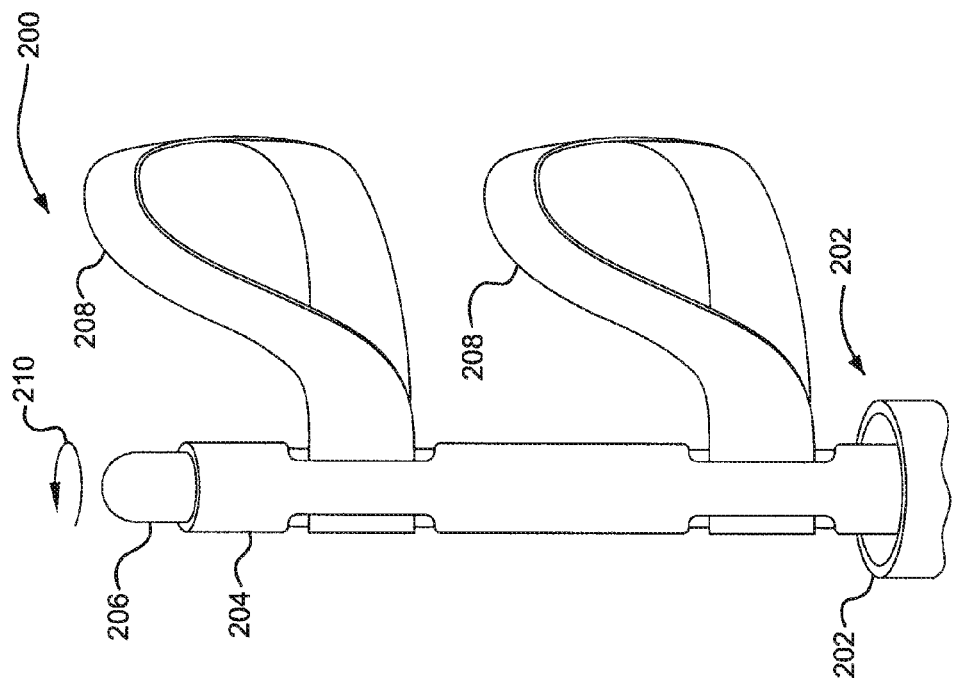
FIGS. 2A and 2B are a medical apparatus according to an aspect of the invention, having flexible straps connected to a torsional member.
Figure 2A:
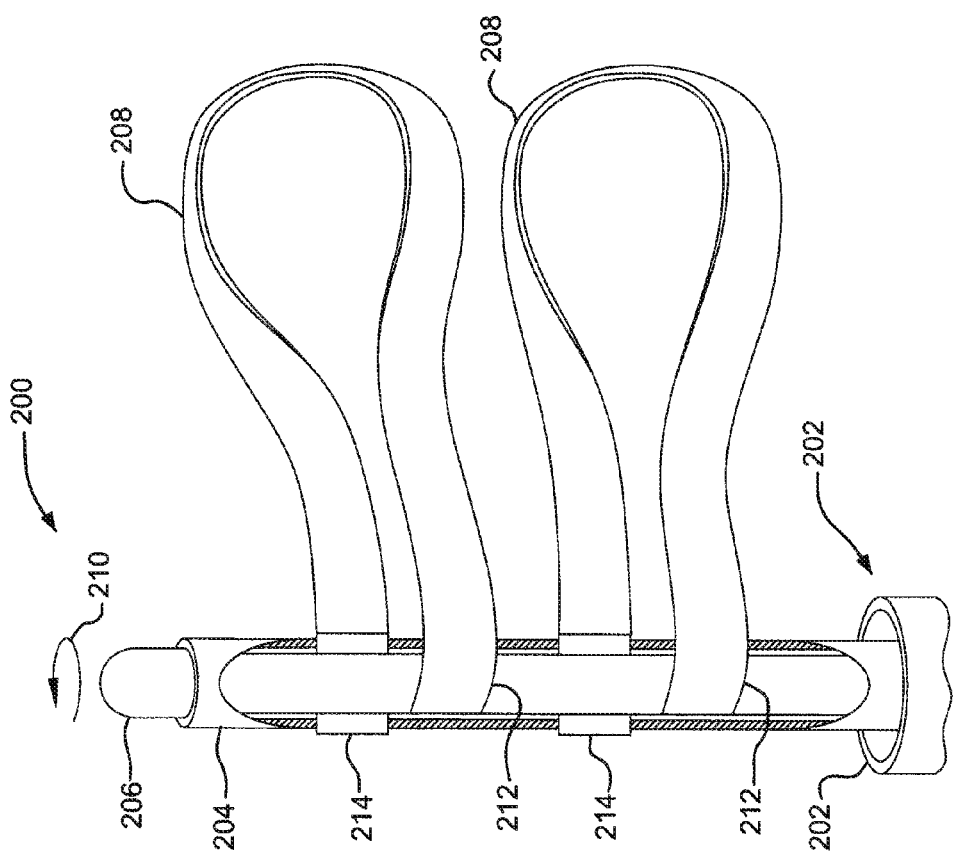

FIGS. 2A and 2B are partial views of the proximal end of a medical apparatus according to a further embodiment of the invention, having releasable straps that can radial compress a stent/graft.

Referring to FIGS. 2A and 2B, the medical apparatus is generally depicted as reference numeral 200. The medical apparatus of FIGS. 2A and 2B is similar to the medical apparatus as shown in FIGS. 1A through 1C with a stent/graft not shown for clarity.

Shown in FIG. 2A is a partial cross-section of a distal end of a catheter system 200 having an outer tube 202. Contained within the outer tube 202 are a first inner tube 204 and a torsional member 206. Attached to the torsional member is at least one flexible strap 208. The flexible strap 208 surrounds a distal portion of a stent/graft (not shown). When the torsional member 206 is rotated as depicted by arrow 210 the strap 208 is further wound around the torsional member 206, thereby "drawing in" the strap which will in turn, compress a surrounded stent/graft. The degree of stent/graft compression can be controlled by varying the amount of twist imparted to the torsional member. A first end 212 of a flexible strap 208 can be affixed to the torsional member 206. The second end 214 of the strap 208 can be wrapped around the torsional member. When the medical apparatus is properly positioned with a target site, the torsional member can be rotated in a direction opposite that shown by arrow 210. This opposite rotation will allow the stent/graft to fully expand. Further opposite rotation of the torsional member will cause the strap end 214 to "un-wind" from the torsional member. The torsional member can then be withdrawn in a distal direction, pulling the strap with attached end 212 into the first inner tube. In an alternate method the first inner tube and the torsional member can be withdrawn together or all three members (204, 206, 208) can be withdrawn together.

Shown in FIG. 2B is a non cross-sectional perspective view of the distal end of the catheter system shown in FIG. 2A. The flexible straps 208 can be fabricated from various bio-compatible materials as commonly known in the art.

Figure 3A:
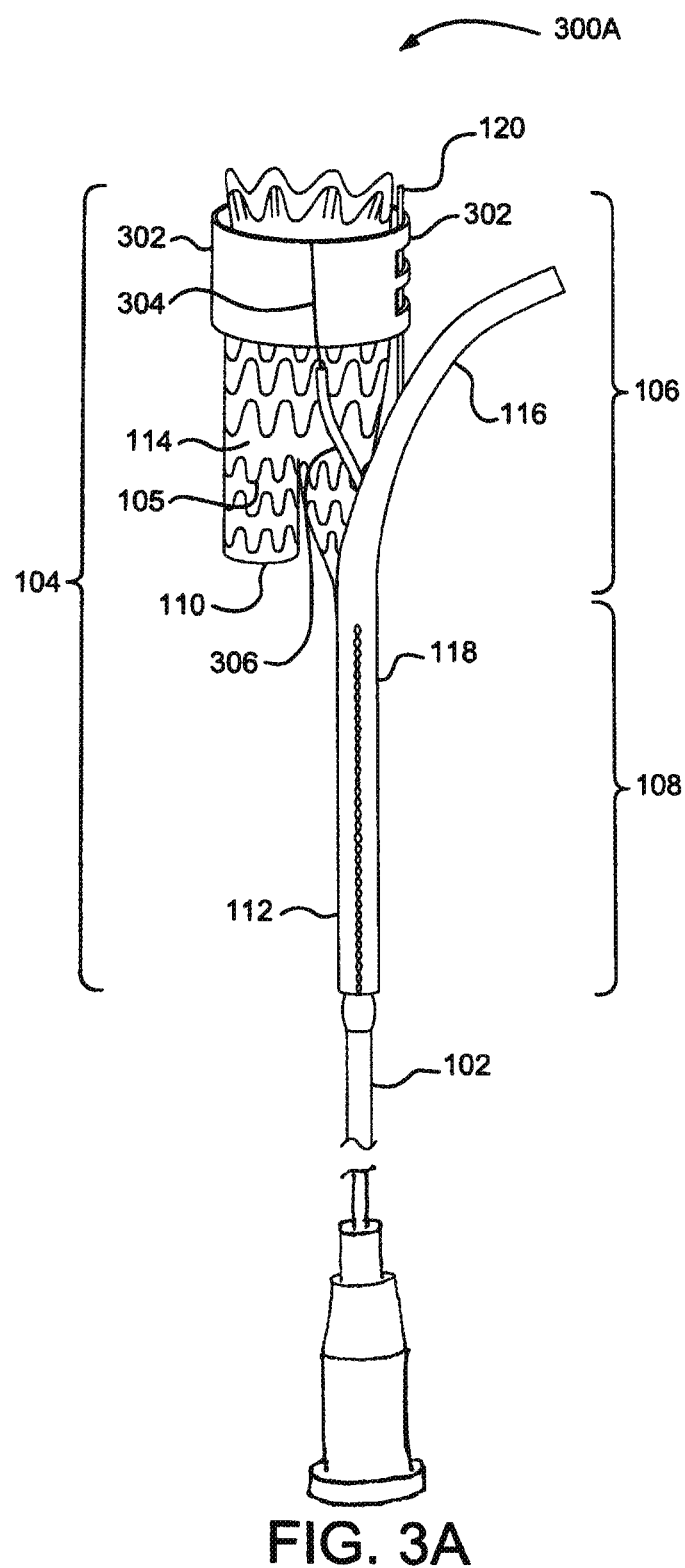
FIG. 3A is a medical apparatus according to an aspect of the invention, having an external torsional member connected to a flexible sleeve with a rip cord.
Figure 3B:
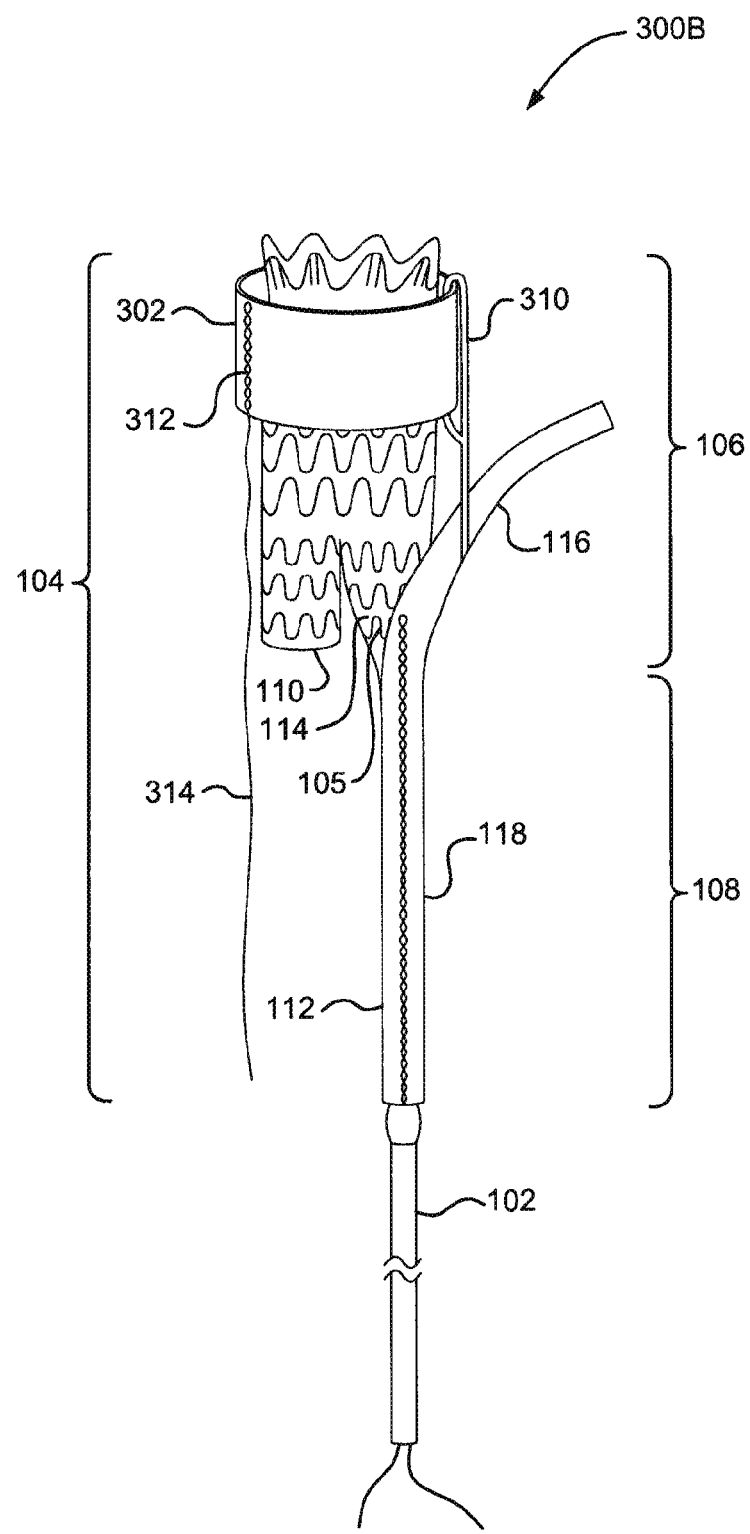
FIG. 3B is a medical apparatus according to an aspect of the invention, having an internal torsional member connected to a flexible constraining sleeve with a parting line.

FIGS. 3A and 3B are partial perspective views of a medical apparatus according to a further embodiment of the invention.

Referring to FIGS. 3A and 3B, the medical apparatus is generally depicted as reference numeral 300A or 300B. The medical apparatus 300A and B includes catheter assembly 102, stent 104 arranged on the proximal end portion of the catheter assembly 102. The stent 104 has an inner surface, an outer surface, and is configured from multiple turns of an undulating element 105. The undulating element 105 can be configured, for example, in a ring or helical pattern.

The stent 104 has a proximal end portion 106 and distal end portion 108. The distal end portion 108 is formed into a branch having a first leg 110 and a second leg 112.

A graft member 114 is arranged about the stent 104.

The stent 104 and graft member 114 are constrained into a compacted delivery state by a first sheath 116 and second sheath 118.

As shown in FIGS. 3A and 3B, the first sheath 116 has been released allowing at least a portion of the stent 104 to expand as shown. The second sheath 118 is coupling the second leg 112 to the catheter assembly 102 as shown.

Shown in FIG. 3A is a flexible constraining sleeve 302, surrounding a proximal portion of the stent/graft. A torsional member 120 extends from a proximal end portion to a distal end portion of the catheter assembly 102. In the figure, the torsional member 120 is positioned adjacent the outer surface of the stent 104 and graft 114. The torsional member 120 is attached to the catheter assembly 102 and not attached to the stent 104 or graft 114. The flexible sleeve 302 is attached to the torsional member 120 so that when the torsional member 120 is rotated, the flexible sleeve is compressed which in turn compresses the stent/graft. The flexible sleeve 302 is shown having a parting or rip cord 304. The rip cord 304 can be in the form of a thread or wire that is contained within a secondary tube 306. The secondary tube 306 can exit the distal end of the catheter assembly 102 with the rip cord exiting the distal end of the secondary tube. When the medical apparatus is properly deployed the distal end of the rip cord can be tensioned, thereby ripping or separating the flexible sleeve 302. Since the flexible sleeve is still attached to the torsional member 120, the flexible sleeve 302 can then be withdrawn along with the catheter assembly 102.

Shown in FIG. 3B is a flexible constraining sleeve 302, surrounding a proximal portion of the stent/graft. A torsional member 310 extends from a proximal end portion to a distal end portion of the catheter assembly 102. In the figure, the torsional member 310 is positioned adjacent the outer surface of the stent 104 and graft 114. The torsional member 310 is attached to the catheter assembly 102 and not attached to the stent 104 or graft 114. The flexible sleeve 302 is attached to the torsional member 310 so that when the torsional member 310 is rotated, the flexible sleeve is compressed which in turn compresses the stent/graft. The flexible sleeve 302 is shown having a parting line 312. Shown is a stitched parting line 312 similar to those parting lines incorporated into the first 116 and second 118 sheaths. The release of the stitched parting line 312 can be activated by a release cord 314. The release cord 314 can be in the form of a thread or wire and can be contained within a secondary tube (not shown) or be contained within a catheter system lumen. The release cord 314 can exit the distal end of the catheter assembly 102. When the medical apparatus is properly deployed the distal end of the release cord 314 can be tensioned, thereby un-stitching or separating the flexible sleeve 302. Since the flexible sleeve is still attached to the torsional member 310, the flexible sleeve 302 can then be withdrawn along with the catheter assembly 102.

It will be apparent to those skilled in the art that various modifications and variation can be made in the present invention without departing from the spirit or scope of the invention. Thus, it is intended that the present invention cover the modifications and variations of this invention provided they come within the scope of the appended claims and their equivalents.

We claim:

1. An apparatus, comprising:
    a catheter having a proximal end portion and a distal end portion;
    a tubular stent graft arranged on the proximal end portion of the catheter, the stent graft having an inner surface and an outer surface;
    a movable element having a first end and a second end; and
    a torsional member rotatably coupled to the catheter, the movable element forming a loop that extends circumferentially about and entirely externally of at least a portion of the stent graft and extending through the torsional member such that the first and second ends extend from opposing sides of the stent graft before extending through the torsional member and exiting a distal end thereof, wherein rotation of the torsional member in a first direction tightens the loop and thereby radially compresses at least a portion of the stent graft, and wherein rotation of the torsional member in an opposite second direction loosens the loop and thereby allows radial expansion of the portion of the stent graft, both the movable element and torsional member being separable from the stent graft to allow withdrawal of both the movable element and torsional member with the catheter from the stent graft.

2. The apparatus of claim 1, wherein movable element extends through a lumen in the torsional member.

3. The apparatus of claim 2, wherein the torsional member includes a side opening from which the loop extends and engages the stent graft.

4. The apparatus of claim 1, wherein the distal end portion of the torsional member extends to at least the distal end portion of the catheter.

5. The apparatus of claim 1, wherein the movable element comprises a filament.

6. The apparatus of claim 5, wherein the filament comprises a wire.

7. The apparatus of claim 5, wherein the filament comprises a polymer.

8. The apparatus of claim 7, wherein the polymer comprises a fluoropolymer.

9. The apparatus of claim 8, wherein the fluoropolymer comprises polytetrafluoroethylene.

10. The apparatus of claim 9, wherein the polytetrafluoroethylene comprises expanded polytetrafluoroethylene.

11. The apparatus of claim 5, wherein the stent graft comprises a stent having an inner surface and an outer surface and a graft member arranged about the stent along at least one of the inner and outer surfaces of the stent, wherein the filament is arranged circumferentially around the stent graft.

12. The apparatus of claim 1, wherein the torsional member extends along an outer surface of the stent graft.

13. The apparatus of claim 1, wherein the movable element comprises a strap having opposite first and second ends.

14. The apparatus of claim 13, wherein the first end of the strap is affixed to the torsional member.

15. The apparatus of claim 14, wherein the second end of the strap is wrapped about the torsional member.

16. The apparatus of claim 15, wherein the loop is formed between the first and second ends of the strap.

17. The apparatus of claim 16, wherein the strap comprises expanded polytetrafluoroethylene.

18. An apparatus, comprising:
    a catheter having a proximal end portion and a distal end portion;
    a tubular stent graft arranged along the proximal end portion of the catheter;
    a movable element forming a loop that extends circumferentially about and entirely externally of a portion of the stent graft;
    a torsional member extending along an exterior of the stent graft, the torsional member being rotatable relative to the stent graft in a first direction to tighten the loop and radially compress the portion of the stent graft about which it is looped and in an opposite second direction to loosen the loop to allow radial expansion of the portion of the stent graft about which it is looped; and
    a releasable constraining sheath that extends along the stent graft and the torsional member and constrains the stent graft in a compacted delivery state.

* * * * *